United States Patent
Farné et al.

(12) 
(10) Patent No.: US 6,536,597 B1
(45) Date of Patent: Mar. 25, 2003

(54) METHOD AND DEVICE FOR ON-LINE CONTROLLING GREEN TIRE MANUFACTURING COMPONENTS

(75) Inventors: Maurizio Farné, Aprilia (IT); Paolo Straffi, Rome (IT)

(73) Assignee: Bridgestone Corporation, Tokyo (JP)

( * ) Notice: Subject to any disclaimer, the term of this patent is extended or adjusted under 35 U.S.C. 154(b) by 27 days.

(21) Appl. No.: 09/656,060

(22) Filed: Sep. 6, 2000

(30) Foreign Application Priority Data

Sep. 7, 1999 (IT) ........................................ TO99A0749

(51) Int. Cl.⁷ ............................. B07C 5/14; G01R 31/08
(52) U.S. Cl. ...................... 209/520; 209/517; 209/518; 209/519; 324/525; 324/534; 324/755
(58) Field of Search ................................ 324/525, 534, 324/755

(56) References Cited

U.S. PATENT DOCUMENTS 3,670,615 A   6/1972  Scholl 4,068,168 A   1/1978  Boonstra

FOREIGN PATENT DOCUMENTS

| EP | 0 252 228 | 1/1988 | | |
|----|-----------|--------|---|---|
| EP | 0 490 838 | 6/1992 | | |
| FR | 2 149 045 | 3/1973 | | |
| JP | 62-7533   | * 1/1987 | ............ | G01B/7/30 |
| JP | 7-209229  | * 8/1995 | ............ | G01N/27/04 |
| JP | 7-209229  | * 11/1995 | ............ | G01N/27/04 |
| WO | WO 83 03675 | 10/1983 | | |
| WO | WO 94/00769 | * 1/1994 | ............ | G01R/27/14 |

* cited by examiner

*Primary Examiner*—Donald P. Walsh
*Assistant Examiner*—Jonathan R. Miller
(74) *Attorney, Agent, or Firm*—John M Vasuta; Michael Sand

(57) ABSTRACT

A method and device whereby green tire components are on-line controlled as to quality, dimensions and structure by means of electric resistance measurements.

12 Claims, 3 Drawing Sheets

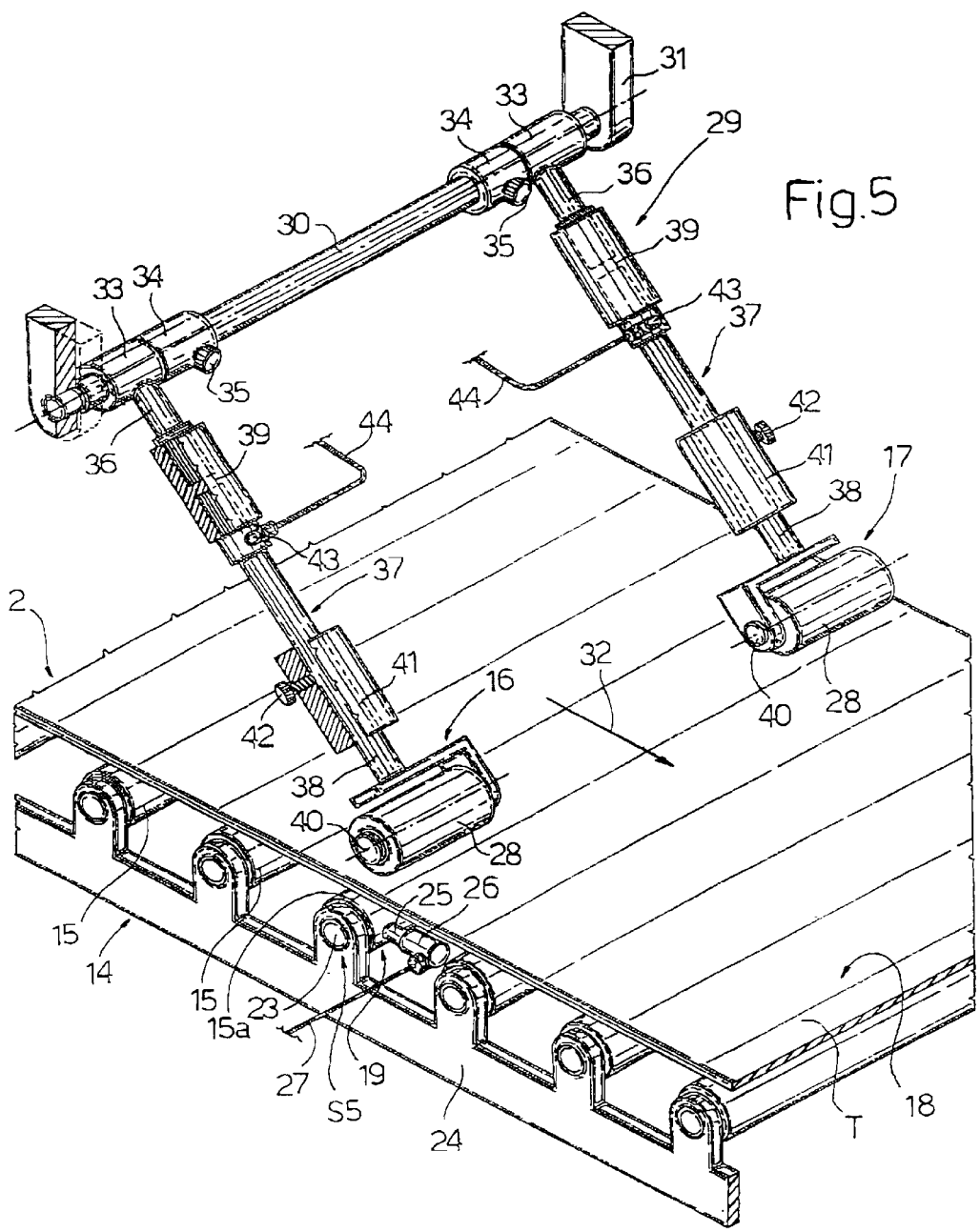

METHOD AND DEVICE FOR ON-LINE CONTROLLING GREEN TIRE MANUFACTURING COMPONENTS

The present invention relates to a method of on-line controlling tire manufacturing components.

More specifically, the present invention relates to a method of on-line controlling the quality, dimensions and structure of green road vehicle tire components.

BACKGROUND OF THE INVENTION

In the road vehicle tire manufacturing industry, green components are first produced in forming devices and then processed and assembled into tires, which are then cured in respective molds.

To ensure conformance of the tires to given specifications, the green components from the forming devices are normally on-line quality controlled to ensure the respective mixes are as required, i.e. are such as to impart the required physical characteristics to the components. As it is processed and fed to the tire assembly machine, each component normally also undergoes various other on-line controls: identification control to identify and ensure the component being supplied is the one actually required; quality control to ensure given physical characteristics (elasticity, hardness, etc.) of the component; dimensional control to ensure the shape and dimensions of the component and/or the shape, dimensions and location of part of the component are as required; and structural control to ensure a given distribution of material within the component (no porosity, etc.).

On known tire manufacturing lines, all these controls are performed using various types of equipment normally comprising laser beam devices (such as the one described in U.S. Pat. No. 5537207) and optical and continuous weighing devices, all of which are capable of controlling dimensional characteristics, but not material quality.

SUMMARY OF THE INVENTION

It is an object of the present invention to provide a method of on-line controlling tire manufacturing components, designed to eliminate the aforementioned drawbacks.

According to the present invention, there is provided a method of on-line controlling tire manufacturing components, whereby at least two distinct points of a said component are placed in contact with respective terminals having different electric potentials to generate an electric current between said two points; said electric current being measured to determine the value of an electric resistance of said component between said two points; and said electric resistance value being compared with at least one reference value.

When the two points, for example, are located a given distance apart, it is possible to determine the electric resistance value of the material of which the component is made, and, by comparing this value with a number of reference values (specific to the material), to determine the type of component and the percentages and dispersion of carbon black and carbon aggregates within the material.

When controlling, for example, a component, the specific electric resistance of the material of which is known by being determined beforehand using the above method, it is possible, by determining, again using the above method, the electric resistance between two given points on the component, and comparing the resistance value with a number of reference values, to determine fairly accurately the distance between the two contact points (thus enabling dimensional control of the component) and also the presence of any air pockets and/or porosity between the two points and within the component.

Finally, when the component being checked contains, for example, portions with specific characteristics, e.g. highly electrically conductive portions for grounding static, determining the electric resistance between specific points on the component provides for determining the presence or absence and the extension of the portion in question.

In each case, given a specific tolerance range about each reference value, comparing the measured resistance value with the reference value or values therefore provides for determining acceptance or rejection of the component, and whether any intervention is required on the production line.

In other words, the above method provides for performing a sort of tire production line check-up by means of controls which may be all or for the most part resistive, i.e. mostly of the same type, and wherein all the controls of the same type may possibly be performed using one control device.

The present invention also relates to a device for on-line controlling tire manufacturing components.

According to the present invention, there is provided a device for on-line controlling tire manufacturing components, the device comprising at least two terminals which are placed in contact with respective distinct points of a said component; an electric circuit connecting said terminals to each other; a voltage source located along said circuit to maintain said two terminals at different electric potentials; current-measuring means located along said circuit to determine the value of an electric resistance of said component between said points; and comparing means connected to said current-measuring means to compare said electric resistance value with at least one reference value.

BRIEF DESCRIPTION OF THE DRAWINGS

A non-limiting embodiment of the present invention will be described by way of example with reference to the accompanying drawings, in which:

FIG. 5 shows a schematic, larger-scale, partially sectioned view in perspective of a detail in FIG. 3.

DETAILED DESCRIPTION OF THE INVENTION

Figure 1:
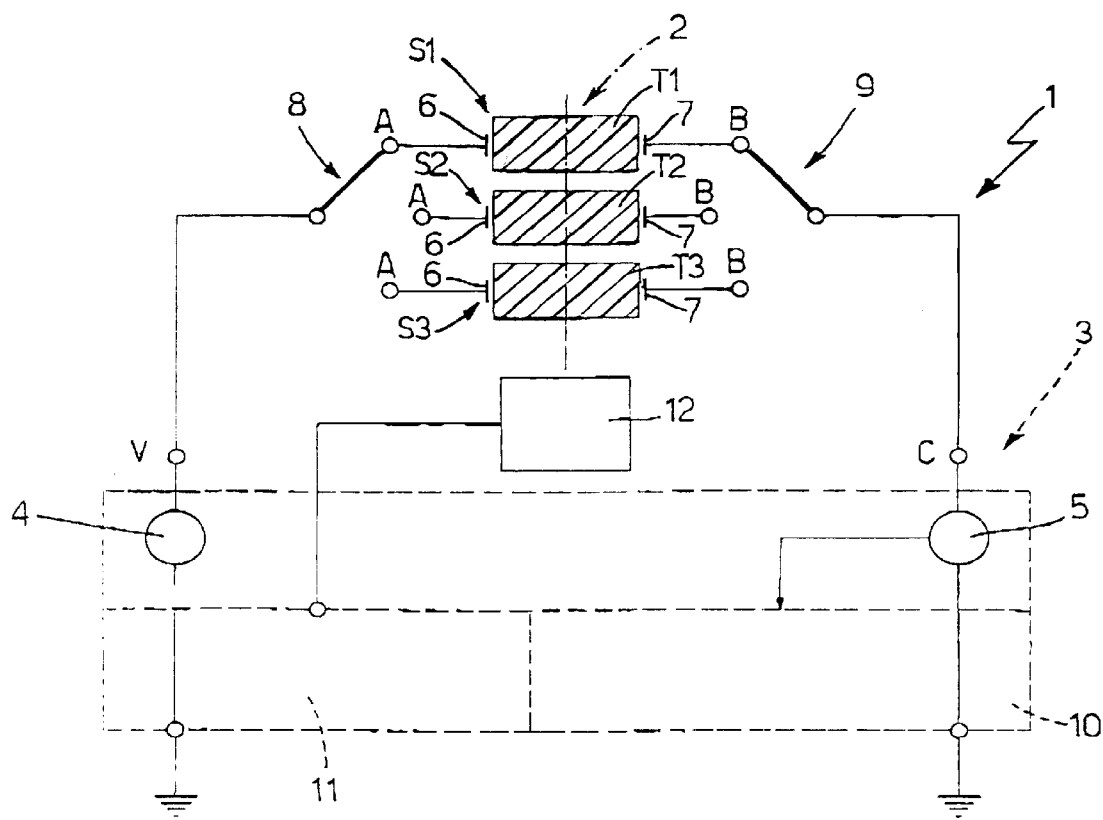
FIG. 1 shows a circuit diagram of a device in accordance with the present invention, for controlling a tire manufacturing line.

Number 1 in FIG. 1 indicates as a whole a control device for a line 2 for producing and assembling components T from which to produce green tires (not shown). (In the example shown, the components considered, which may also be preassembled, are, purely by way of example, three in number and indicated T1, T2, T3).

Line 2 extends through a number of control stations S (in the example shown, control stations S are one for each component T and indicated S1, S2, S3, though, in actual fact, a given component may undergo two or more controls in a number of stations S coinciding spatially with one another);

and control device 1 comprises a measuring unit 3 for measuring the electric resistance between two terminals indicated V and C.

Measuring unit 3—for example, a commercially marketed HEWLETT PACKARD HP4439B measuring unit—comprises a voltage source 4 (for generating an adjustable constant direct voltage) having a grounded first terminal and a second terminal connected to terminal V; and an ammeter 5 having a first terminal connected to terminal C and a grounded second terminal.

Ammeter 5 is connected (in known manner not shown) to voltage source 4 to determine the voltage value applied to terminal V with respect to the ground potential, and so calculate the resistance value between terminals V and C by applying Ohm's law (R=V/I). Ammeter 5 also provides for controlling voltage source 4 in known manner, to vary the voltage applied to terminal V with respect to the ground voltage as a function of the resistance between terminals V and C, and so keep the current value within the instrument reading range. Measuring unit 3 is thus able to measure widely differing resistance values (within a measuring range of 1 to $10^{16}$ Ohms) while maintaining a relatively high degree of precision.

Each control station S comprises a pair of terminals—in particular, an input terminal A and an output terminal B—which have respective terminals 6 and 7 connectable electrically to distinct points of relative component T. Control device 1 comprises two switches 8 and 9 (preferably known and electronically controlled) connected to terminals V and C respectively, and for selectively connecting each pair of terminals A and B to measuring unit 3.

Finally, control device 1 comprises a known comparator 10 for comparing a resistance value, measured by ammeter 5, with one or more reference values; and a processor 11 which dialogs with comparator 10 to supply comparator 10 with the reference value (stored in a nonvolatile memory and established on the basis of calibration readings of specimen components) and receive back the measured and reference value comparison result.

Processor 11 is connected to and supplies a control unit 12 of line 2 with commands as a function of the result of said comparison (or the results of a number of comparisons). More specifically, processor 11 supplies control unit 12 with a command to reject component T, a command to stop operation and request the presence of an operator, or a command to vary the parameters of the operations performed on line 2.

Control stations S are arranged in series along production line 2, and each control a particular characteristic of a respective component T by measuring the electric resistance between two given points of the component T. To measure the resistance between two given points of a component T at a control station S, terminals 6 and 7 of station S are connected—as described later on—to the given points of component T and, at the same time, switches 8 and 9 are operated to connect the pair of terminals A and B of station S to terminals V and C of measuring unit 3.

By way of example, at control station S1, respective terminals 6 and 7 are connectable to given points located a given distance apart on the same surface, preferably the upper surface, of a respective component T. On the basis of the resistance value measured between the two points, processor 11 is able to determine the resistivity value or specific electric resistance of the material of component T, and, by comparing this value with a number of reference values, to determine the type of component in question and the percentages and dispersion of carbon black and carbon aggregates within the material.

By way of a further example, at control station S2, respective terminals 6 and 7 are connectable to given points on different surfaces of a respective component T; and, from the resistance value measured between the two given points, and the specific electric resistance value of the material of component T (measured at the previous control station S1), processor 11 is able to determine the distance between the two contact points (thus enabling dimensional control of the component) and, by comparison with reference values, the presence of any air pockets and/or porosity between the two given points and within component T.

By way of yet a further example, at control station S3, respective terminals 6 and 7 are connectable to given points on opposite surfaces—in particular, on a top and bottom surface—of a respective component T; and, on the basis of the resistance value measured between the two given points, processor 11 is able to determine whether component T contains portions with specific characteristics, e.g. highly electrically conductive portions within or on the surface of substantially insulating or semiconducting materials for grounding static.

In an alternative embodiment not shown, at least one of control stations S1, S2, S3 is replaced by a control station (not shown) having three pairs of terminals 6 and 7, and which, when supplied with a component T, successively performs the above three measurements by operating switches 8 and 9, or may perform only one or two of the above measurements, depending on the type of component T.

Figure 2:
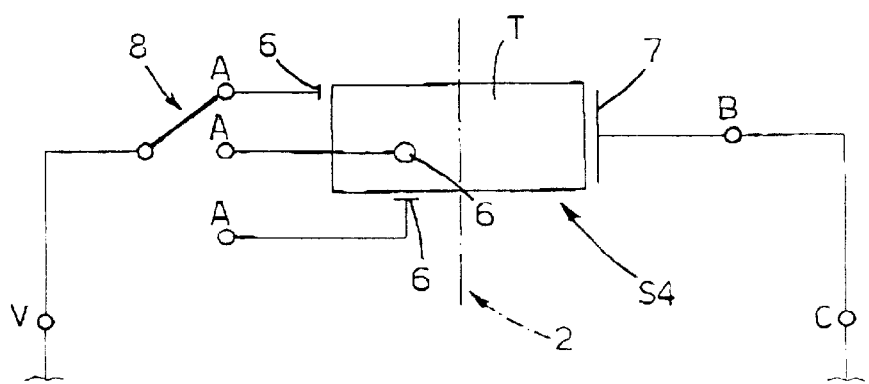
FIG. 2 shows a circuit diagram of a variation of a control station of the FIG. 1 device.

In the FIG. 2 embodiment, control stations S1, S2, S3 are replaced by one control station S4 having three different terminals 6 connected to respective terminals A connectable to terminal V of measuring unit 3 by switch 8, and one terminal 7 permanently connected to terminal C of measuring unit 3. When supplied with a component T, control station S4 successively performs the above three measurements by appropriately operating switch 8, or may perform only one or two of the above measurements, depending on the type of component T.

Figure 3:
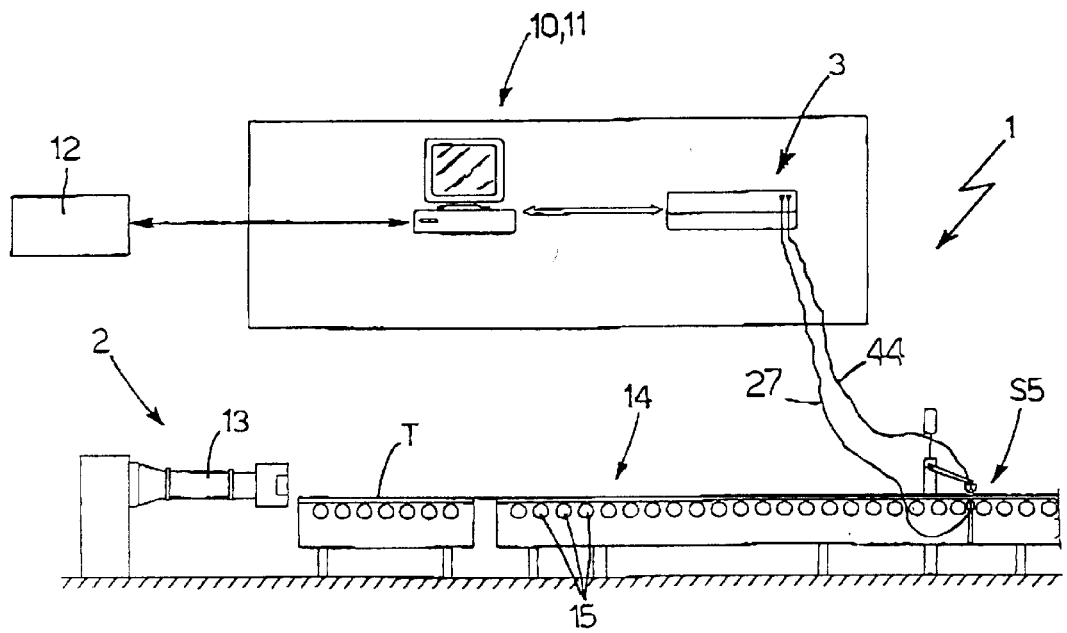
FIG. 3 shows a schematic lateral elevation of a particular embodiment of the FIG. 2 control station.
Figure 4:
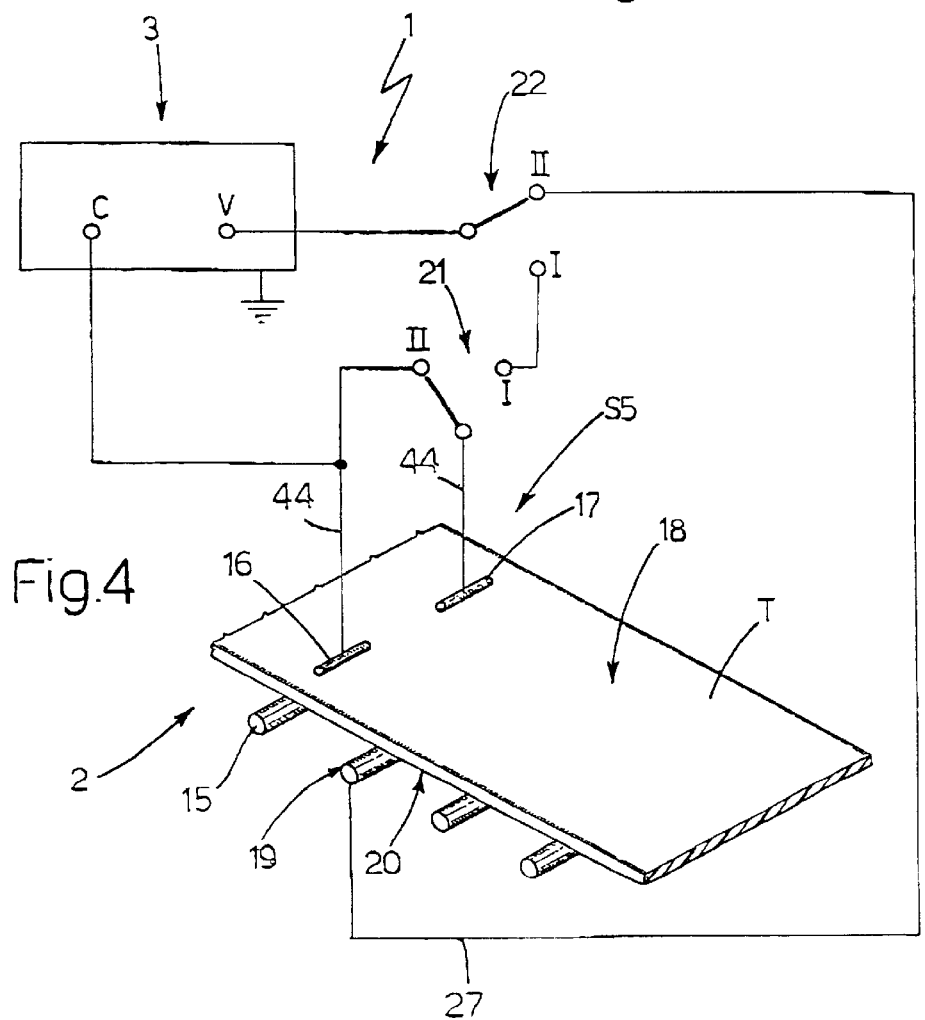
FIG. 4 shows a circuit diagram of the FIG. 3 control station.

In the embodiment shown in FIGS. 3–5, control device 1 comprises one control station S5 in which two different measurements may be performed on a respective component T, in particular a continuous strip of extruded green tread.

As shown in FIG. 3, production line 2 comprises a known extruder 13, which feeds component T onto a roller conveyor 14 for feeding component T to successive known work stations (not shown) and comprising a number of equally spaced horizontal rollers 15. Some of rollers 15 are powered (in known manner not shown) to impart a forward movement to component T, while the other rollers 15 are mounted idly to simply support component T. Control station S5 is located along conveyor 14, with the electric connections shown in FIG. 4, and the mechanical structure shown schematically in FIG. 5.

As shown in FIG. 4, control station S5 comprises two terminals 16 and 17 electrically connectable to a top surface 18 of component T; and a terminal 19 defined by a respective idle roller 15 connectable electrically to a bottom surface 20 of component T.

Terminal 16 is connected permanently to terminal C of measuring unit 3; terminal 17 is connectable selectively to terminal C or V of measuring unit 3 by two known switches 21 and 22; and terminal 19 is connectable to terminal V of measuring unit 3 by switch 22. More specifically, when switches 21 and 22 are set to a first position indicated I in FIG. 4, terminal 17 is connected to terminal V and terminal 19 is disconnected to perform a first resistance measurement of component T between two points on surface 18; when switches 21 and 22 are set to a second position indicated II in FIG. 4, terminal 17 is connected to terminal C in parallel with terminal 16, and terminal 19 is connected to terminal V, to perform a second resistance measurement of component T between a point on surface 18 and a point on surface 20.

The second measurement measures the electric resistance between a point, on bottom surface 20 of component T, contacting terminal 19, and two points, on top surface 18 of component T, contacting terminals 16 and 17. In alternative embodiments not shown, the resistance of a component T is measured between a first set of points on the same or different surfaces and contacting first terminals connected in parallel, and a second set of points on the same or different surfaces and contacting second terminals connected in parallel.

With reference to FIG. 5, at least the roller 15 defining terminal 19 (and indicated 15a) is a metal roller fitted to a respective shaft 23, the opposite ends of which project outwards of roller 15a and engage in rotary manner respective holes formed in two beds 24 (only one shown in FIG. 5) made of electrically insulating material to electrically insulate roller 15a; and roller 15a is connected electrically by a known sliding contact 25 to a terminal 26 in turn connected to switch 22 by an electric cable 27.

Terminals 16 and 17 are defined by respective rollers 28 made of conducting material, preferably metal, and fitted idly to a support 29, which comprises a rod 30 maintained by a frame 31 in a horizontal position perpendicular to the traveling direction 32 of component T along roller conveyor 14. Support 29 also comprises two cylindrical sleeves 33, each fitted in rotary and axially-sliding manner to rod 30 and having a respective lock sleeve 34, which is fitted in rotary and axially-sliding manner to rod 30, is connected in rotary and axially-fixed manner to respective sleeve 33, and has a respective radial through screw 35 for axially locking lock sleeve 34 along rod 30.

Each sleeve 33 is connected integrally to an end portion 36 of a respective arm 37 extending radially outwards with respect to relative sleeve 33 and comprising a further end portion 38 made of electrically conducting material. End portion 38 is connected integrally to end portion 36—also made of electrically conducting material—by an intermediate portion 39 made of electrically insulating material, and supports a respective roller 28 in rotary manner by means of a respective transverse shaft 40 parallel to rod 30.

A respective counterweight 41 of given weight is fitted in sliding manner along each arm 37, comprises a respective lock screw 42 by which it is locked axially to respective arm 37, and provides for imparting to respective arm 37 a given downward torque about rod 30.

In actual use, rollers 28 are pressed, at constant, adjustable pressure, against top surface 18 of component T by the combined weight of arms 37, which is mainly due to the mass of counterweights 41.

End portion 38 of each arm 37 is fitted with a terminal 43, which is connected to measuring unit 3 (terminal 16) or to switch 21 (terminal 17) by a respective electric cable 44 (shown in FIGS. 3 and 4).

To ensure a continuous reading, a cylindrical terminal has been found to be most effective, with the lateral surface being brought into contact with component T. For which reason, terminals 16, 17, 19 in FIGS. 5, 6, 7 are advantageously, though not necessarily, defined by cylindrical rollers.

In a preferred embodiment not shown, cables 27 and 44 are shielded cables to reduce the effect of electromagnetic noise on the resistance measurements performed by measuring unit 3.

What is claimed is:

1. A method of on-line controlling a plurality of different tire manufacturing components (T), said method including the steps of:

placing a pair of terminals (V, C) in contact with respective distinct points on a first of said components (T), said terminals having different electric potentials;

applying a voltage (V) to one of said terminals for generating an electric current between the said distinct points on the first of said components (T);

measuring the electric current between said terminals to determine the value of an electric resistance of said first component (T) between the distinct points;

comparing the electric resistance of said first component with at least one reference value;

placing a pair of terminals (V, C) in contact with respective distinct points on a second of said components (T);

switching the voltage (V) to one of said terminals of said second component for generating an electric current between the said two points on the second of said components (T);

measuring the electric current between said terminals of said second component to determine the value of an electric resistance of said second component (T) between the two points; and comparing the electric resistance of said second component with at least one reference value.

2. A method as claimed in claim 1, wherein said first and second components are rejected on the basis of the result of said comparisons.

3. A method as claimed in claim 1, wherein operating parameters of a production line (2) producing said components (T) are varied on the basis of the result of said comparisons.

4. A method of on-line controlling a tire-manufacturing component (T), said method including the steps of:

placing a first pair of terminals (V, C) each in contact with a respective distinct point of a pair of distinct points on said component (T), said terminals having different electric potentials;

applying a voltage (V) to one of said terminals for generating an electric current between said first pair of distinct points;

measuring the electric current between said terminals to determine the value of a first electric resistance of said component (T), said first electrical resistance being indicative of a first characteristic of said component (T);

comparing the first electric resistance with at least one reference value;

switching the pair of terminals into contact with a second pair of distinct points on said component (T);

applying a voltage (V) to one of said terminals for generating an electric current between said second pair of distinct points;

measuring the electric current between said terminals to determine the value of a second electric resistance of said component (T), said second electrical resistance being indicative of a second characteristic of said component (T); and comparing the second electrical resistance with at least one reference value.

5. The method as claimed in claim 4 wherein one of the first and second characteristics is a physical characteristic of the component.

6. The method as claimed in claim 4 wherein one of the first and second characteristics is a dimensional characteristic of the component.

7. The method as claimed in claim 4 wherein one of the first and second characteristics is a structural characteristic of the component.

8. A device for on-line (2) controlling a plurality of tire manufacturing components (T), the device comprising:

a first pair of terminals placed in contact with respective distinct points on a first of said components (T);

an electric circuit (4, 5, 8, 9) connecting said first pair of terminals to each other;

a voltage source (4) located along said circuit (4, 5, 8, 9) to maintain said first pair of terminals at different electric potentials;

current-measuring means (5) located along said circuit (4, 5, 8, 9) for determining the value of an electric resistance of said first component (T) between said points;

comparing means (10) connected to said current-measuring means (5) for comparing the value of said electric resistance of said first component with at least one reference value;

a second pair of terminals placed in contact with respective distinct points on a second of said components (T) and connected together by said electric circuit; and switching means for switching said electric circuit between said first and second pairs of terminals.

9. A device as claimed in claim 8, where each of said terminals comprises a cylindrical body (15a, 28) and a lateral surface which is in contact with said component (T).

10. A device as claimed in claim 9, wherein each said cylindrical body (15a, 28) is mounted to rotate idly on a respective support (29); said cylindrical body (15a, 28) being electrically insulated from said support (29), and being connected electrically to said current-measuring means (5).

11. A device as claimed in claim 8, wherein said device (1) is located along a conveyor (14) conveying said components (T); and wherein the conveyor (14) comprises a succession of rollers (15) for supporting said components (T) with one (15a) of said rollers (15) being one of said first pair of terminals.

12. A device for on-line (2) controlling a tire manufacturing component (T), the device comprising:

a pair of terminals placed in contact with a first pair of respective distinct points on said component (T);

an electric circuit (4, 5, 8, 9) connecting said pair of terminals to each other;

a voltage source (4) included in said circuit (4, 5, 8, 9) for determining the value of an electric resistance of said component (T) between said first pair of distinct points;

comparing means (10) connected to said current-measuring means (5) for comparing the value of said electric resistance with at least one reference value;

a second pair of terminals placed in contact with a second pair of respective distinct points on said component (T) for connection together by said electric circuit; and switching means for switching said electric circuit between said first and second pairs of terminals.

* * * * *